United States Patent [19]

Bellon

[11] Patent Number: 5,403,456
[45] Date of Patent: Apr. 4, 1995

[54] DEVICE PERMITTING THE SPREADING OF ONE OR SEVERAL REAGENTS ON A GEL

[75] Inventor: Franck Bellon, Longjumeau, France

[73] Assignee: Sebia, Issy les Moulineaux, France

[21] Appl. No.: 904,377

[22] Filed: Jun. 25, 1992

[30] Foreign Application Priority Data

Jun. 28, 1991 [FR] France ................. 91 08122

[51] Int. Cl.[6] ................. G01N 27/26; G01N 27/447; B05C 5/00; B01D 1/26
[52] U.S. Cl. .................. 427/2.11; 204/180.1; 204/299 R; 204/182.8; 118/401; 427/256
[58] Field of Search ............. 204/182.8, 299 R, 180.1; 427/2, 256; 118/401

[56] References Cited

U.S. PATENT DOCUMENTS

| | | | |
|---|---|---|---|
| 3,428,547 | 2/1969 | Zec | 204/182.7 X |
| 3,844,918 | 10/1974 | Cawley | 204/182.8 |
| 4,177,038 | 12/1979 | Biebricher et al. | 8/192 |
| 4,919,784 | 4/1990 | Yetman | 204/299 R |

FOREIGN PATENT DOCUMENTS

| | | |
|---|---|---|
| 0043287 | 6/1982 | European Pat. Off. . |
| 0092295 | 10/1983 | European Pat. Off. . |
| 2316992 | 4/1977 | France . |
| 3900272 | 7/1990 | Germany . |
| 57-146145 | 9/1982 | Japan ............. 204/182.8 |
| 1360844 | 7/1974 | United Kingdom . |
| WO85/04256 | 9/1985 | WIPO . |

OTHER PUBLICATIONS

CA99(18):146159z "Coating of Activated Carton for Medical Use", Oct. 1983.
A. J. Crowle "Templates for Antiserum Application in Immunoelectrophoresis and Two-Dimensional Electroimmunodiffusion", Journal of Immunological Methods vol. 14 (1977) 197-200.

*Primary Examiner*—John Niebling
*Assistant Examiner*—John S. Starsiak, Jr.
*Attorney, Agent, or Firm*—Zarley, McKee, Thomte, Voorhees & Sease

[57] ABSTRACT

The invention relates to a rigid mask intended for the deposition, spreading and incubation of one or several liquids on a gel (of total surface Sg) according to one or several well-defined zones of the gel, hereafter designated by "incubation surface Si", this mask comprising:

an upper surface which is in particular flat and a lower surface which is in particular flat, in particular substantially parallel to each other, at least one orifice intended to permit deposition and spreading of the liquid on the incubation surface Si of the gel, and at least one slit crossing the mask over the whole of its thickness and intended to permit withdrawal of the excess of liquid present on the incubation surface Si of the gel, the lower surface of the mask being intended to be deposited in proximity to the surface Sg of the gel, under conditions such that the lower surface of the mask is not in contact with the incubation surface Si.

Application to the development of a gel previously subjected to the electrophoresis of proteins.

13 Claims, 10 Drawing Sheets

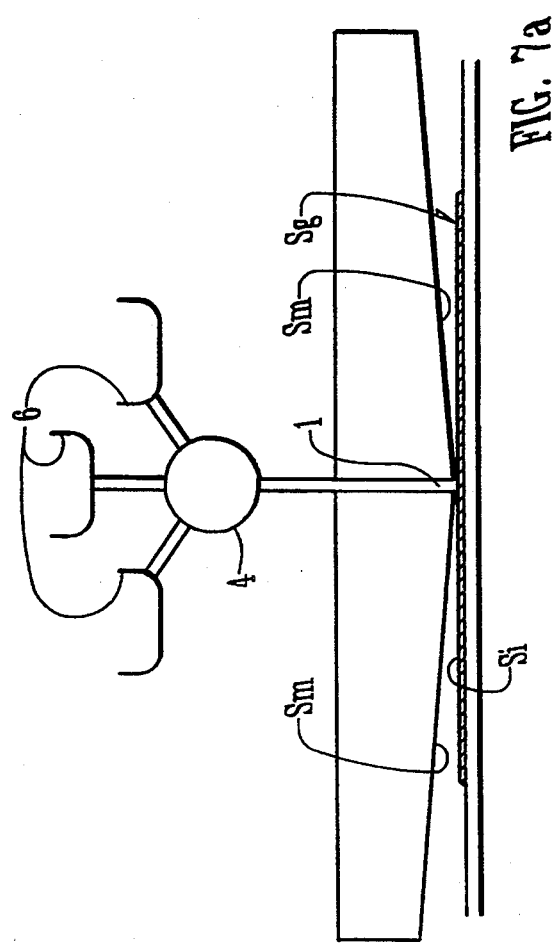

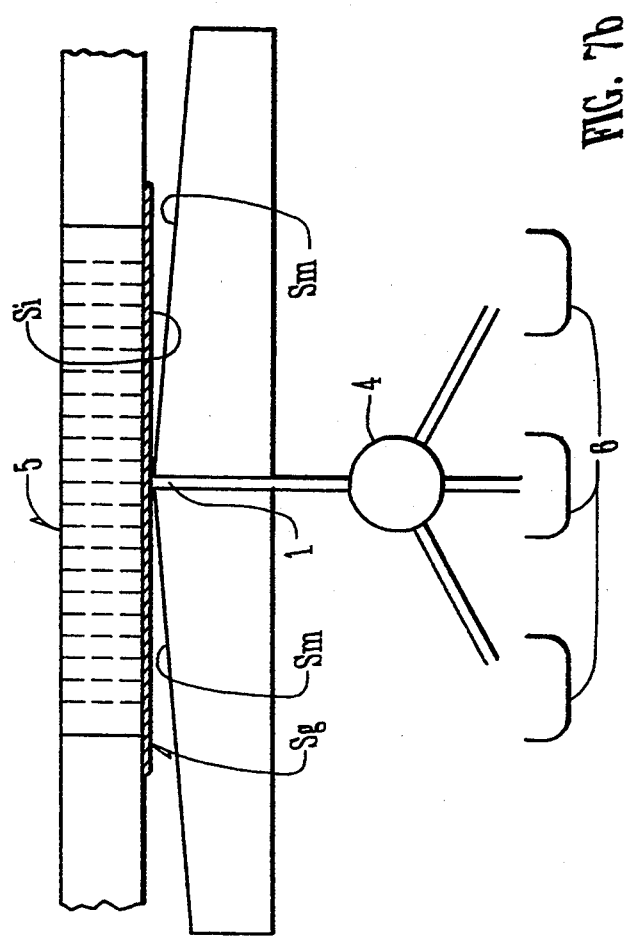

DEVICE PERMITTING THE SPREADING OF ONE OR SEVERAL REAGENTS ON A GEL

BACKGROUND OF THE INVENTION

The invention relates to a device permitting the spreading of one or several reagents on a gel, in particular an electrophoresis or immunofixation gel.

The invention also relates to a method making use of the aforementioned device.

Electrophoresis is the migration of suspended or colloidal particles in a liquid or a gel, due to the effect of potential difference across immersed electrodes. Migration is toward electrodes of charge opposite that of the particles.

Electrophoresis is useful in the study of proteins because the protein molecules act like colloidal particles, their charge being positive or negative depending upon whether the surrounding solution is acidic or basic. Therefore, the acidity of the solution can be varied by the introduction of one or more reagents and used to control the direction in which a protein moves upon electrophoresis. Furthermore, different protein particles in a mixture move toward the electrodes with different velocities depending upon the number of charges carried by the particles. The techniques of electrophoresis or immunofixation are usually followed, after the migration, by a stage of incubating the gel with a reagent in order to detect and possibly to quantify the protein fractions separated during the electrophoresis.

The most conventional case is the staining of the set of protein fractions separated by electrophoresis by means of a dye which becomes bound specifically on to the latter. In this case, the reagent used (the dye) is a product which is generally cheap and of which it is possible to prepare a solution in a sufficient quantity to immerse the gel totally therein.

However, this method cannot be envisaged in the case where it is necessary to use small quantities of reagent, when it is an expensive reagent, or when it is desired to produce on the same gel incubations on discrete zones with different reagents.

These possibilities relate for example to assaying isoenzymes contained in a serum (isoLDH, isoCK, isophosphatase) where the gel is incubated with a substrate (expensive product) for these enzymes with the aim of forming a colored or fluorescent product which permits quantification by densitometry.

The case where it is necessary to carry out, on the same gel, incubations with different reagents is constituted for example by immunofixation where various discrete zones of the gel must be incubated with various antisera of different specificity (expensive reagent) and a protein fixative.

In all these cases, use of a minimum quantity of reagent is sought.

In implementing the abovementioned methods, a sheet of filter paper cut to the size of the gel is impregnated with a quantity of reagent just sufficient for it to be entirely moistened and it is then applied to the surface of the gel.

In the case where various reagents are possibly used on distinct zones of the same gel, as many strips of filter paper are cut as there are zones to be covered by the various reagents, and these various strips are impregnated with the various reagents before being applied to the various zones where the incubation is to take place.

This method has a certain number of drawbacks. It is in fact necessary to avoid trapping air bubbles between the gel and the sheet of filter paper impregnated with reagent, because, in the region of the air bubbles, the reaction would not take place for lack of reagent on the gel. The paper being opaque, it is sometimes difficult to detect the presence of these air bubbles.

Moreover, during the incubation reaction, a proportion of the proteins which it is desired to develop can be absorbed onto the paper, or more simply be absorbed by pumping onto the latter.

If an extended incubation time is necessary (30 minutes to 1 hour), this phenomenon is accentuated by the fact that, during the incubation, evaporation from the free surface of the paper occurs. The latter having a tendency, by capillarity, to maintain a constant degree of humidity, a flow of liquid is created, from the gel to the paper, with entrainment of the protein fractions to be assayed initially contained in the gel. This leads to a loss of sensitivity of the development on the gel and, this absorption not being very homogeneous, quantification by densitometry of the developed fractions risks being subject to errors.

Furthermore, and above all, this is a manual process which is very laborious and therefore difficult to implement in routine clinical analysis, and, in current practice, has been abandoned.

Another method also used consists in using a mask constituted by a sheet of flexible plastic, preferably hydrophobic in nature, having approximately the same external outline as the gel and having one or more independent openings of rectangular shape. This mask, once applied to the gel, delimits the zone or zones intended to receive the reactant or reactants.

Use of such a mask also has a certain number of drawbacks.

After electrophoretic migration, it frequently happens that a proportion of the liquid exudes from the surface of the gel. This exudation is mainly created by electroendosmotic flow.

Before applying the mask to the gel, it is necessary to remove this excess liquid by pumping by means of a thin filter paper, because, if liquid is still present on the gel, it prevents good adhesion of the mask to the gel, as well as a good seal at the periphery of the zone(s) delimited, being assured.

As well as the additional manual operation of pumping, the filter paper risks entraining a portion of the proteins from the gel and of distorting the result.

Furthermore, the gel or the reagents used can, in certain cases, contain surfactants which will facilitate insertion of liquid between the gel and the mask and, under certain conditions, even after removal of the excess liquid which has exuded from the gel at the end of migration, the mask risks not assuring the required seal.

With this type of mask, it is important that the whole of the surface of the mask is perfectly applied to the gel. It is necessary to avoid trapping air bubbles between the gel and the plastic mask during its positioning on the gel. Otherwise, there is a risk of having either a leak of reagent under the mask, or a mixing of adjacent reagents.

An object of the present invention is to propose a device which largely overcomes the preceding drawbacks.

The subject of the present invention is a device permitting deposition, spreading and incubation of a reagent on a gel, in which quantities of reagent of the same order of magnitude as those of conventional devices are used, the device of the invention being however without the drawbacks of the conventional devices.

Another object of the present invention is to propose a device permitting deposition, spreading and incubation of a reagent on a gel, in which it is possible to incubate different zones with respectively different reagents, without there being mixing of the reagents.

The aim of the present invention is to propose a device permitting deposition, spreading and incubation of a reagent on a gel, in which manual operations are limited to the minimum.

An object of the present invention is to propose a device for deposition, spreading and incubation of a reagent on a gel, permitting accurate results to be obtained as to quantification of the substances fractionated in the gel.

An object of the present invention is to propose a device for deposition, spreading and incubation of a reagent on a gel, capable of being automated.

SUMMARY OF THE INVENTION

The subject of the invention is a rigid mask whose intended use is for the deposition, spreading and incubation of one or more liquids on a gel (of total surface area Sg) according to one or more well-defined zones of the gel, hereafter designated by "incubation surface Si", this mask comprising:
- an upper surface and a lower surface, the distance separating the lower surface and the upper surface constituting the thickness of the mask,
- a smooth useful surface portion Sm on the lower surface of the mask delimited by surface irregularities such as grooves and steps which constitute obstacles to the spreading of liquid by capillary action outside of Sm
- at least one orifice intended to permit deposition and spreading of the liquid on the incubation surface Si of the gel, and constituted by a hole through the thickness of the mask, and/or
- at least one slit through the thickness of the mask, this slit being intended to permit withdrawal of any excess liquid present on the incubation surface Si of the gel, this slit having an opening intersecting the useful surface portion Sm and disposed opposite the incubation surface Si so as to be in fluid communication therewith,
- at least two stops on the lower surface for positioning the mask so that at least 0.1 millimeters separates the incubation surface Si of the gel from useful surface portion Sm.

This mask only allowing the liquid to spread on the surface Si of the gel which is a projection of Sm, this projection of Sm on the gel being greater than or equal to the area of the incubation surface Si of the gel.

The invention advantageously permits placing of the mask above a gel having incubation surface or surfaces thereon. It is also possible to position the mask below the incubation gel with its "lower" position surface facing upwardly. In either case, the surface of deposition, spreading and incubation of the reagents on the gel is situated in proximity to, but spaced apart from the opposing "lower" surface of the mask.

BRIEF DESCRIPTION OF THE DRAWINGS

FIG. 6a shows a flat mask lower surface parallel to a horizontal gel surface at a distance e.

FIG. 6b shows the gel/mask set of FIG. 6a inclined upwardly from horizontal at the orifice end.

FIG. 6c shows the mask inclined while the gel remains horizontal.

FIG. 6d shows the lower mask surface inclined with respect to the upper mask surface which is parallel to the gel surface.

FIG. 6e shows two lower mask surfaces with an angle therebetween.

FIG. 6f shows a gel/mask set having angled lower mask surfaces as in FIG. 6e, but having an incubation surface which stops at the intersection of the angled mask surfaces.

FIG. 6g shows a lower mask surface having a concave or radiused surface at one end.

FIG. 6h shows a lower mask surface which is concavely curved.

FIG. 6i shows a lower mask surface which is convexly curved.

FIGS. 7a, 7b and 7c show masks having lower surfaces inclined away from the surface of the gel.

FIG. 7a illustrates a gel/mask set in which a single orifice serves the functions of both deposition orifice and a slit for withdrawal of excess reagent. The gel is shown to be located above the lower surface of the mask.

FIG. 7b shows the mask positioned below the gel which is held thereabove by a vacuum means.

FIG. 7c illustrates a gel/mask device permitting deposition, spreading and incubation of one or more reagents on several distinct incubation surfaces Si of the gel.

DETAILED DESCRIPTION OF THE INVENTION

The liquid is generally the reagent intended to develop the proteins which have previously been deposited on the gel. The reagent is introduced via the through hole 1 defined hereinabove, (FIG. 1A) which will also be termed "deposition orifice".

In FIGS. 1-7, the incubation surface Si is the zone of the gel which it is essential to cover with the reagent (or reagents) in order that development of the proteins should take place. The length of the incubation surface, that is to say the dimension of the incubation surface parallel to the direction of electrophoretic migration, is designated by Li (FIGS. 6a-6i).

In the case of a single reagent, Si can be equal to the area Sg (FIGS. 3a and 3b) or else Si can be a mere portion of Sg (Si<Sg as in FIGS. 4a, 4b, and 4c) including nevertheless the set of migration tracks, that is to say the zones of the gel where the electrophoretic separations have taken place.

Figure 6A:
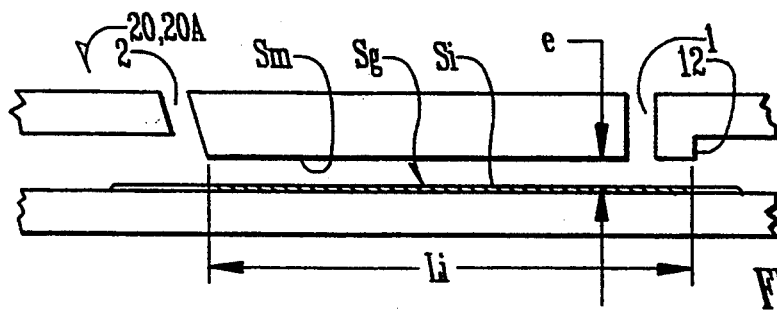
FIGS. 6a–6i are cutaway views showing various ways to configure the lower surface of the mask and position it with respect to the gel to achieve capillary action and spreading of the reagent.
Figure 6B:
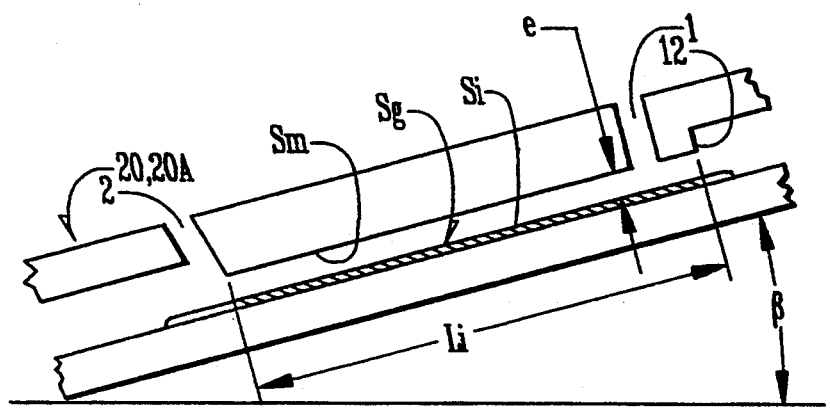
Figure 6C:
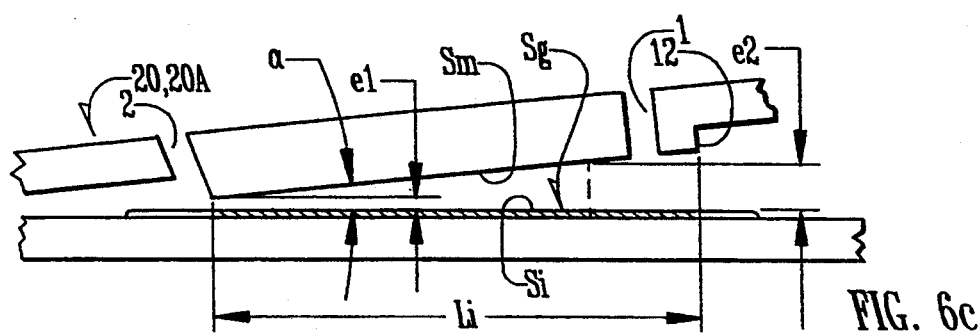
Figure 6D:
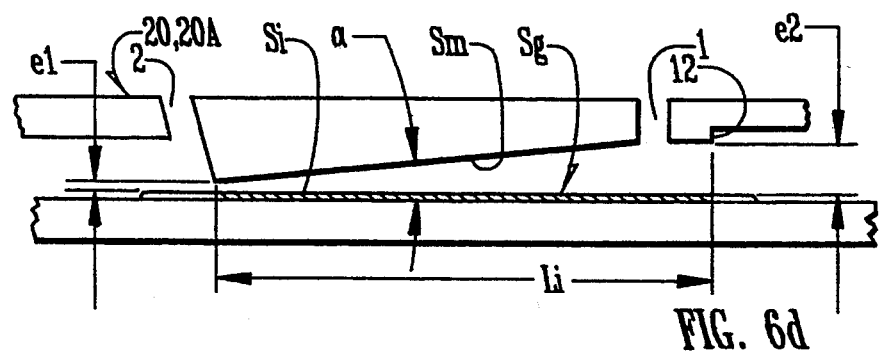
Figure 6E:
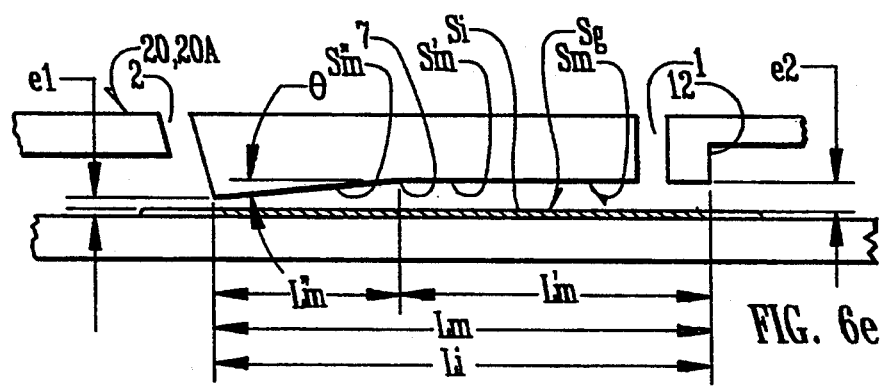
Figure 6F:
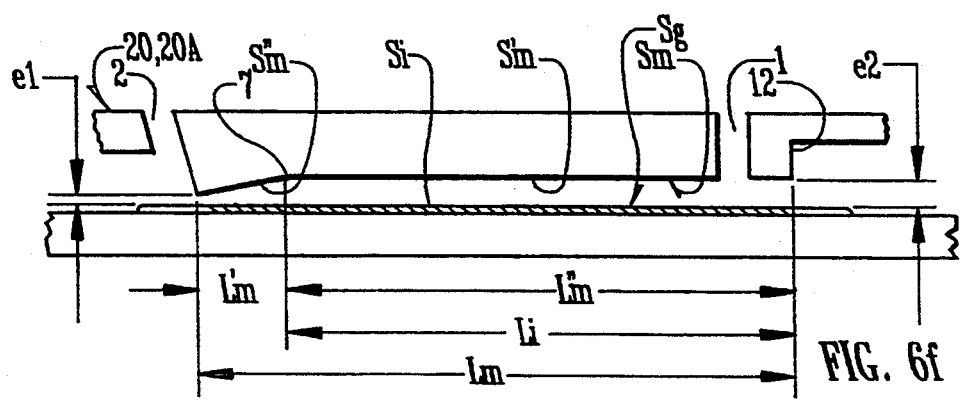

It is necessary however to note that the zone effectively covered by the reagent can be greater than the area Si (cf. FIG. 6f).

FIGS. 2, 5a, 5b, and 7c show the case of incubation with different reagents, or possibly with the same reagent but on distinct zones of the gel, including for example each of the various migration tracks, the incubation surface of the gel is defined by $Si_1$, $Si_2$, $Si_n$, n being an integer equal to or greater than 2.

Figure 6G:
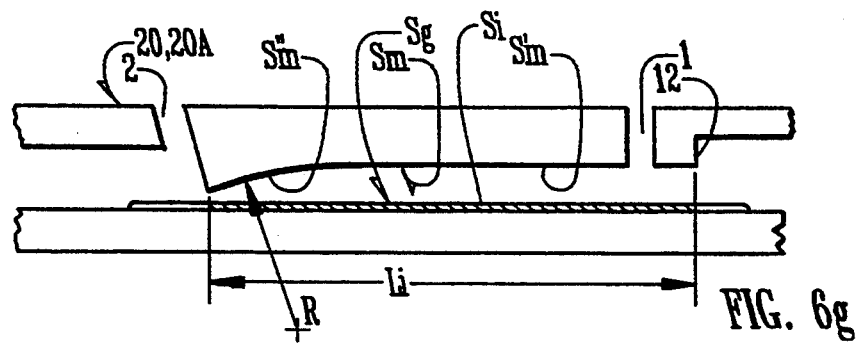

The useful surface portion of the lower surface of the mask is designated by "Sm" (FIGS. 1, 1A, 2, 2C and 2D). Sm is essentially smooth and has no irregularity on its surface capable of constituting an obstacle to the spreading of the reagent on the incubation surface Si, and in particular neither concave roughness, nor convex roughness, that is to say a surface without a ridge or a hollow which would be capable of preventing the reagent from spreading on the surface Si. As long as it meets the above requirements this surface Sm can be flat (FIGS. 1A, 2D, 6a-d), curved (FIGS. 6g-i), or some combination of flat or curved elements (FIGS. 6e, 6f and 6g).

The surface Sm can include the slit 2 and deposition orifice 1 defined hereinabove.

Advantageously, the surface Sm is flat or curved, in particular cylindrical, with a radius which is large with respect to the dimensions of Si.

As shown in FIG. 6e and 6f, the surface Sm can also be composed of elementary facets, which are flat or curved, in particular cylindrical, connected together, these various facets, as well as their connections, being such that there is no obstacle to the spreading of the liquid on the incubation surface Si.

The length Lm is the dimension of the surface Sm parallel to the direction of electrophoretic migration. The width of the surface Sm, which is dealt with hereinbelow, corresponds to the dimension perpendicular to the length defined hereinabove.

When this surface Sm having a deposition orifice 1 permitting deposition of a reagent is positioned in proximity with the surface of a gel, it must make it possible to keep by capillarity, between itself and the surface Si to be incubated, a reagent introduced via the deposition orifice 1.

This deposited liquid can then spread between Sm and the surface of the gel until it encounters a discontinuity 3, such as the edge of the gel, or the edge of the mask, or a groove, or a concave difference in height like a step 12 which delimits the surface Sm.

Spreading of the liquid is taken to mean advance or displacement of the liquid on the surface Si, due only to capillary forces (resulting from the proximity of the lower surface of the mask and the incubation surface Si) and possibly the force of gravity.

In the case where several reagents must be spread, the mask surfaces are defined by $Sm_1$, $Sm_2$, $Sm_n$, n being an integer equal to or greater than 1. As previously discussed, as these surfaces can be flat, curved, cylindrical, coplanar, cocylindrical or composed of connected elementary facets which are flat, curved, or cylindrical.

Surfaces $Sm_1$, to $Sm_n$ are delimited by concave differences in height or grooves 3.

Slit 2 this can be situated in the mask such that its projection is on the incubation surface Si or outside the incubation surface Si, as long as it intersects for fluid communication therewith one of the edges of the said incubation surface Si, or one of the edges of the surface effectively covered by the reagent. Advantageously, the slit is adjacent to the edge of the surface Si opposite the deposition orifice 1 (FIGS. 6a-c).

Generally, the slit is preferably situated outside the incubation surface Si (FIGS. 6a-6i). In fact, if it is situated in the incubation surface Si, it must have dimensions such that it is not capable of being an obstacle to the spreading of the liquid. Under these conditions, the slit is narrow (less than or equal to approximately 1 mm) and makes it possible to keep by capillarity an excess of reagent.

The topography of the upper surface of the mask is a variable parameter. However, the upper surface is advantageously flat. In the text that follows, in order to simplify the description, it will be considered that the upper surface is flat, and that the useful lower surface Sm, of length Lm

- either is substantially parallel to the upper surface (FIGS. 6a-c),
- or forms with the upper surface, when the latter is used horizontally, an angle $\gamma$ which is less than approximately 3° (FIG. 6d),
- or else is substantially parallel to the upper surface over a part of its length L'm and over the rest of its length L"m, in the extension of the parallel surface, forms an angle with the upper surface, this angle being such that it is not capable of preventing spreading of the liquid on the incubation surface Si (FIG. 6e).

In the third case mentioned hereinabove relating to the position of the lower surface with respect to the upper surface, the lower surface is preferably substantially parallel to the upper surface over a part of its length Lm which corresponds to the length of the incubation surface Li. The extension of this parallel surface S'm by a part S"m forming an angle with the upper surface is advantageously such that the angle between the lower surface and the gel is an acute angle of approximately 1° to approximately 90°, which will favor removal of the excess of reagent in the vicinity of the slit if the angled part of the lower surface most closely approaches the gel.

The surface Sm of the mask can also be curved, preferably cylindrical.

When the surface of the mask is constituted by a cylindrical surface, it is necessary for its diameter to be greater than or equal to the square of Li.

When the cylindrical surface only relates to a fraction f of the incubation length Li, the diameter must be greater than or equal to the square of the length f×Li.

Figure 2:
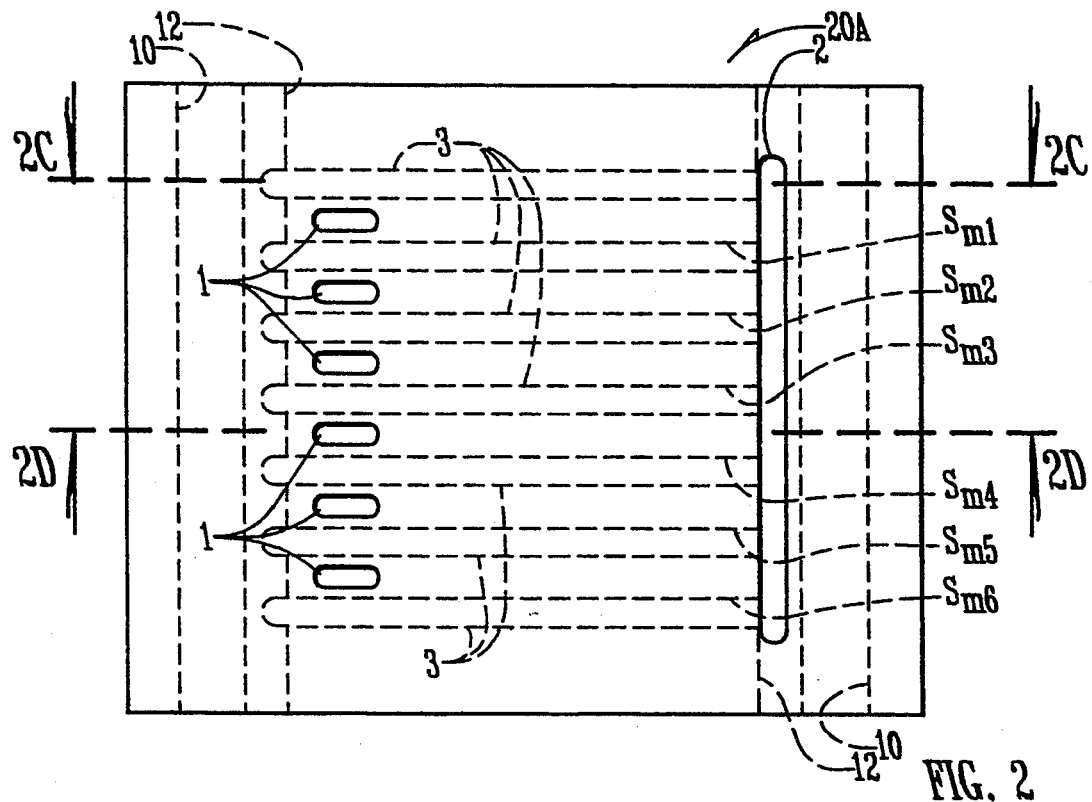
FIG. 2 is a plan view of the mask of this invention showing several distinct useful surface portions Sm of the mask.

As shown in FIG. 2, the invention also relates to a mask intended for deposition, spreading and incubation of one or several liquids, in which the lower surface of the mask comprises at least two differences in height or two grooves 3, the differences in height or grooves being spaced apart from each other in order to delimit at least a part of the mask Sm, which part does not include any irregularity on its surface capable of being an obstacle to the spreading of the liquid on an incubation surface Si, and whose projection on a gel is equal to or greater than the area of the incubation surface Si of the gel on which surface the liquid can be spread, the differences in height and the grooves having a height sufficient for the liquid to be able to be kept by capillarity on the aforesaid incubation surface Si of the gel.

In this embodiment of the invention, the part Sm of the mask is limited neither by the edge of the gel, nor by the edge of the mask, but by at least two differences in height or two grooves, which have a height sufficient, and possibly a width sufficient, for the liquid to be able to be kept by capillarity on the aforesaid incubation surface Si of the gel and not to go beyond the limits of the incubation surface Si of the gel or the limits of the projection of the surface Sm on the gel.

The grooves can cross the whole of the mask, and they will be designated by "hollow grooves". In order for the hollow grooves to keep the liquid by capillarity, it is necessary for their dimensions to be such that they cannot act as a reservoir with possible collection of the liquid within the said reservoir, and therefore that they have advantageously a width greater than or equal to 2 mm, and a height greater than or equal to 0.2 mm, advantageously 0.5 mm and preferably 1 mm.

The differences in height or grooves surround a migration track and are advantageously rectilinear.

In general, the migration tracks have the shape of a rectangular strip, having for example the following dimensions: length of approximately 10 mm to approximately 100 mm, width of approximately 2 mm to approximately 80 mm. When a migration track is surrounded by two grooves, the two other edges of the migration track can be constituted by a part of two of the edges of the gel or of two of the edges of the mask, or by two other grooves perpendicular to the two other grooves previously defined.

When there are several migration tracks, the latter are advantageously such that their edges of smallest dimension are in the same alignment.

The subject of the invention is also a mask intended for deposition, spreading and incubation of a single liquid, comprising a single deposition orifice through the thickness of the mask, intended to permit deposition, spreading and incubation of a single liquid on a gel according to an incubation surface Si of the gel.

This embodiment relates to the case where it is desired to deposit, spread and incubate a single liquid.

In this case, a single through hole is contemplated in order to carry out the deposition of the liquid.

This deposition orifice can have the shape of an elongated slit, having for example the following dimensions: length 50 mm, width 1.5 mm.

The invention also relates to a mask intended for deposition, spreading and incubation
of several liquids on a gel according to respective incubation surfaces $Si_1$ to $Si_n$ or (FIG. 7c) of one liquid on a gel according to several incubation surfaces $Si_1$ to $Si_n$, n ranging from 2 to 50, this mask being such that its lower surface comprises differences in height or grooves, the differences in height or grooves being spaced apart from each other in order to delimit several parts of the mask $Sm_1$ to $Sm_n$, and whose projection on the gel is greater than or equal to the areas of the incubation surfaces $Si_1$ to $Si_n$ of the gel, on which surfaces the liquid is to be spread, the differences in height and the grooves having a height sufficient for the liquid to be able to be kept by capillarity on the aforesaid incubation surfaces $Si_1$ to $Si_n$ of the gel.

This case corresponds to the deposition of several liquids on respective incubation surfaces or of one liquid on several incubation surfaces $Si_1$ to $Si_n$.

To ensure the deposition, spreading and incubation of the liquid on the surface Si, it is possible to envisage the orifice which is used for deposition having a volume such that it is capable of constituting a reservoir having a capacity for retaining the extra liquid in order to assure spreading of the liquid on the incubation surface Si, even if a slight quantity of reagent has evaporated during incubation (cf. FIG. 6a).

It is possible to proceed otherwise in order to assure the deposition, spreading and incubation of the liquid on the incubation surface Si. In fact, if the gel and the mask are kept substantially parallel to each other, it can be useful to incline the gel and mask together by rotation around an axis substantially parallel to one of the edges of the gel or to one of the edges of the mask, so that the liquid descends under gravity in the direction of the incubation surface Si which is to be covered (cf. FIG. 6b).

It is also possible, in order to assure the deposition, spreading and incubation of the liquid, to keep the gel in a substantially horizontal position and slightly to incline the mask by rotation around an axis parallel to one of the edges of the mask or to one of the edges of the gel and situated in the vicinity of the edge of the incubation surface so that the distance between the gel and the mask in the region of this axis is smaller than the distance between the gel and the mask in the zone opposite this axis (cf. FIG. 6c).

Given that the capillary forces are greater in the vicinity of this axis, the liquid is distributed by capillarity over the incubation surface Si.

The subject of the invention is also a mask such as previously described in which the deposition orifice has a volume such that it is capable of constituting a reservoir having a capacity for retaining the extra liquid in order to assure spreading of the liquid on the incubation surface Si.

According to an embodiment of the mask of the invention, the deposition orifice has an elongated shape or a circular shape, which is preferably elongated and has advantageously a width of approximately 1 mm to approximately 2 mm, in particular 1.5 mm, and a length of approximately 4 mm to approximately 80 mm, in particular 5 mm.

According to another embodiment, the deposition orifice of the mask is capable of containing by capillarity a volume of liquid at least equal to V/10, V being the volume existing between the incubation surface Si and the mask, when the mask and the gel are positioned respectively one in relation to the other under conditions such that the liquid deposited in the deposition orifice spreads over the gel.

According to another embodiment of the invention, the deposition orifice is situated in the vicinity of the middle of the part Sm of the mask and has the shape of an elongated slit, whose dimensions are such that it cannot prevent the liquid being deposited on the incubation surface Si, and whose length is advantageously the length of the incubation surface Si and whose width is advantageously from approximately 1 mm to approximately 2 mm, this deposition orifice also being capable of assuring the function of the slit intended to permit withdrawal of the extra liquid which is spread on the surface Si.

According to another embodiment of the invention, the slit intended to permit withdrawal of the extra liquid is substantially parallel to the width of the incubation surface and is positioned adjacently to the edge of the incubation surface which is opposite to the vicinity of the deposition orifice, and has advantageously a width of approximately 1 mm to approximately 4 mm, in particular 2 mm, and a length greater than or equal to the width of the surface Si, and the internal peripheral surface of the slit is perpendicular to the surface of the mask and preferably inclined with respect to the perpendicular direction of the surface of the mask in order to permit the placing in direct contact of means permitting withdrawal of extra liquid with the said extra liquid (FIGS. 6a-i).

In order to give an idea, the inclination of the internal peripheral surface of the slit with respect to the direction perpendicular to the surface of the mask can be approximately 30°.

According to another embodiment of the invention, the thickness of the mask is approximately 1 mm to approximately 20 mm, in particular approximately 2 mm to approximately 10 mm, and the differences in height have a height at least equal to 0.2 mm, advantageously approximately 0.5 mm to approximately 20 mm, or the grooves have a width sufficient so that, during incubation, each liquid kept by capillarity between the mask and an incubation surface Si does not mix with the liquids kept in the incubation surfaces which are directly adjacent to Si, the width of the grooves being approximately 1 mm to approximately 10 mm.

According to another embodiment of the invention, the mask comprises several mask parts Sm, advantageously approximately 6 to approximately 50, each of the parts Sm comprising a deposition orifice, preferably situated in the part of Sm whose projection on the gel corresponds to the anodic part of the gel, this mask comprising a single slit intended to permit withdrawal of the extra liquid which is spread on the surfaces Si of the gel, this slit extending preferably perpendicularly with respect to the largest of the dimensions of the parts Sm of the mask and being preferably situated in the mask at a position such that its projection is in the cathodic region of the gel (cf FIG. 2).

The parts Sm are advantageously constituted by rectangles, having for example a length greater than or equal to approximately 10 mm to approximately 80 mm and a width of approximately 2 mm to approximately 80 mm.

The subject of the invention is also a mask as previously described comprising a single part Sm, whose dimensions are greater than or equal to those of Si (FIG. 3a), and comprising in the vicinity of one of its ends a deposition orifice having an elongated shape, whose length corresponds preferably to the width of the incubation surface Si, and also comprising, in the vicinity of the other end, a slit intended for withdrawing the extra liquid, this slit being advantageously, in length, at least the width of Si.

The invention also relates to a mask comprising means for positioning the mask with respect to the gel such that the minimum distance between the gel and the part Sm of the mask is greater than or equal to 0.1 mm, and the value of the maximum distance is approximately 0.5 mm to approximately 2 mm, in particular 1 mm.

These means can be constituted by any fastening means, for example screws etc. It is also possible to envisage the mask including, on its periphery, stops 10 capable of resting on the gel, these stops being positioned and having dimensions such that there is no contact between the part Sm of the mask and the incubation surface Si (cf of FIG. 1A).

According to another advantageous embodiment of the invention, the upper surface of the mask and its lower surface are not parallel to each other, but form an angle such that, when the upper surface of the mask is positioned parallel to the surface of the gel, the minimum distance between the gel and the mask is greater than or equal to approximately 0.1 mm and the value of the maximum distance is approximately 0.5 mm to approximately 2 mm, in particular 1 mm (cf FIG. 6d).

The subject of the invention is also a mask produced so that the orifice for deposition and spreading of the liquid coincides with (is identical to) the slit intended to permit withdrawal of the extra liquid. This embodiment makes it possible in particular to contemplate easier automation of the device for deposition, spreading and incubation of one or several reagents on a gel (cf FIG. 7a-c).

The deposition orifice (1) coincides in this embodiment with the slit for removing the reagents and is connected, by means of pipes and a multichannel valve, to the various reagent solutions to be introduced as well as to a "discharge" flask intended to gather the reagents removed. These solutions are conveyed in one direction or the other by means of a pump.

Under these conditions the distinct slit 2 of the orifice (1), previously described and permitting, after the incubation phase, removal of the reagent by pumping by means of a filter paper introduced in this region, is no longer necessary and is dispensed with.

Under these conditions the orifice (1) can have various shapes, and can preferably have a circular shape of small diameter advantageously less than 2 mm and preferably less than 1 mm.

According to this embodiment in which the deposition orifice is also used to remove the reagents after incubation, it is advantageous that:
1) the periphery of the orifice (1) is the part of the surface Sm of the mask, capable of being in contact with the various reagent solutions, which is nearest to the surface of the gel without however coming into contact with it (minimum separation greater than or equal to 0.1 mm);
2) as the distance from this orifice on the surface Sm becomes greater, the gel/mask separation increases.

In the case where the reagent introduced has cohesive forces similar to those of water the maximum distance between the surface of the gel and that of the mask is not to exceed 2 mm (it being possible for this maximum separation to be slightly increased or reduced if the cohesive forces of the liquid introduced are respectively increased or reduced).

Given the flatness of the gel, the constraints of minimum separation of 0.1 mm in the region of the orifice (1) and on the other hand of maximum separation of approximately 2 mm at the periphery of the incubation zone Si define the shape of the surface Sm of the mask which is for example in a centered or off-centered pyramidal shape with a rectangular or square base, or alternatively in the shape of a centered or off-centered conical surface of revolution with a circular or elliptical base and whose apex corresponds to the orifice (1).

The angles at the apex of this pyramid or of this conical surface of revolution depend on the dimensions of the surface Si of the gel to be incubated.

For example in the case of a circular incubation surface of 90 mm diameter the angle at the apex of a mask having a surface Sm of centered conical shape with a circular base must be between 175° and 179°.

Under these conditions, during the introduction of a reagent brought to the orifice (1) by means of pipes and a pump, the liquid will be distributed on the surface of the gel starting from the orifice (1), the successive outlines of the zones of the gel covered by the reagent being contour lines of equal distance of the surface Sm with respect to the surface of the gel which is kept in a horizontal position. In the case where the surface of the mask is a centered conical surface of revolution with a circular base these will be concentric circles centered on the orifice (1).

It is expedient to introduce the various reagents free from air bubbles (because in the location of an air bubble, the reagent not being in contact with the gel, the incubation will not take place in that region) and at sufficiently slow flow rates of the order of (50 to 1000 $\mu l/s$) in order to avoid damaging the gel facing the orifice (1) in consequence of applying hydraulic pressures incompatible with the mechanical strength of the gel.

After the incubation phase the reagent is recovered via the orifice (1) by means of the pump. The orifice (1) being the surface on the zone nearest to the gel, it is in this region that the capillary forces for the liquid introduced between the mask and the gel will be the maximum, and as the liquid is drawn up the latter will collect in this zone of minimum gel/mask spacing. During this operation, the successive outlines of the zones of the gel still covered with liquid will be in inverse order the same as those obtained during introduction, and correspond to the contour lines of equal distance between the mask and the gel. Insofar as the drawing up of the liquid is sufficiently slow (50 $\mu l$ to 1000 $\mu l/s$) in order not to break the cohesion of the liquid (especially at the end of the drawing up) the latter will be drawn up continuously and practically completely.

In order that removal of the reagent previously introduced should be as complete as possible it is important:

1) that the diameter of the orifice (1) flush with the surface of the mask should be of small size (diameter of the order of 1 millimeter);

2) that it should be at a small distance from the surface of the gel, of 0.1 to 1 mm and preferably of 0.2 to 0.6 mm;

3) in the aim of maintaining cohesion of the last drop which will be drawn up, and it is preferable, that the surface of the mask which surrounds the periphery of the orifice (1) should have a flat surface parallel to the surface of the gel over a zone of 10 to 200 mm², preferably of 25 to 100 mm².

In this embodiment placing of the mask below the surface of the gel can be contemplated.

The gel being kept by an appropriate means (for example by drawing up under vacuum by means of a porous plate as shown in FIG. 7b) in a horizontal position with the free face of the gel directed towards the base of the mask, the gel is then underneath and the operation of the whole is similar to that previously described.

It nevertheless appears under these conditions that the removal of the last drop of liquid previously introduced is facilitated since it has in addition a tendency by gravity to collect in the region of the intake orifice (1).

In the case where a single reagent is introduced according to this method on the same gel it is expedient to calibrate the volume of reagent delivered by the pump in order to cover the zone Si of the gel which is to be incubated.

If the area of the surface Si is equal to the area of the surface of the gel beyond the volume contained between the surface of the gel and the surface of the mask opposite, an excess of reagent will still be kept. Additional extra liquid can nevertheless escape the capillary forces without however entraining the rest of the solution contained between these two gel and mask surfaces. It is sufficient under these conditions to have a recovery system, for example a gutter, at the periphery of the mask with a system for disposal of this extra reagent, in order for it to have no detrimental effect on the development process.

In the case where several different reagents are introduced according to this method onto the same gel it is imperative not to have any mixing of the reagents.

Each of the zones $Sm_1$, $Sm_2$ ... $Sm_i$ of the mask corresponding to the various incubation zones $Si_1$, $Si_2$ ... $Si_i$ of the gel is then in the shape of a pyramid with a rectangular or square base or alternatively of a centered or off-centered conical surface of revolution with a circular, ellipsoidal or rectangular, etc., base each having an orifice (1) at its apex and separated from each other by furrows and all the orifices being situated preferably at the same distance from the gel (cf FIG. 7c).

Independent pumps simultaneously (or successively) inject calibrated volumes of the various reagents via each of the orifices so that the gel surfaces $Si_1$, $Si_2$ ... $Si_i$ are covered.

An excess of reagent can be tolerated insofar as the various surfaces $Sm_1$, $Sm_2$ ... $Sm_i$ are slightly larger than the surfaces $Si_1$, $Si_2$ ... $Si_i$ to be incubated and as the gel/mask spacings in the region of the periphery of the zones $Si_1$, $Si_2$, and $Si_i$ are less than 2 mm (in the case of liquids introduced whose cohesive forces are similar to those of water) in order to permit keeping by capillarity a possible excess of reagent beyond this periphery.

Removal of the reagents after the incubation phase is carried out in the same manner as previously described.

The subject of the invention is also a set comprising a mask and a gel, permitting implementation of an incubation on a gel previously subjected to electrophoresis or permitting crossed (cross-dot) reactions to be carried out.

The subject of the invention is also a set comprising means permitting the parts Sm of the mask to be sufficiently close to the gel for the Liquid intended to be spread on the incubation surfaces Si to be kept by capillarity on the incubation surfaces Si of the gel in projection of the parts Sm of the mask and for the parts Sm of the mask to be parallel to the gel or to be inclined with respect to the gel, preferably according to an angle of approximately 0.5 to approximately 3°, advantageously of approximately 1.5°, the minimum distance between the mask and the gel being advantageously in the vicinity of the slit and the maximum distance between the mask and the gel being advantageously in the vicinity of the deposition orifice (cf FIGS. 6c–f).

The invention also relates to a method of deposition, spreading and incubation of one or several liquids on a gel (of surface Sg) according to one or several well-defined zones of the gel, hereafter designated by "incubation surface Si", characterized in that a mask is positioned, according to the invention, with respect to the gel, so that the part Sm of the mask should be sufficiently close to the incubation surface Si for the liquid intended to be spread on the surface Si to be kept by capillarity on the said surface Si, and in that:

the liquid is introduced into the deposition orifice defined hereinabove, the mask is kept with respect to the gel in the position as indicated hereinabove, or, if the mask and the gel are parallel to each other, the mask in inclined with respect to the gel in order that the liquid should be distributed by capillarity on the surface Si, or the gel and mask set is inclined with respect to the horizontal (cf FIG. 6b) so that the liquid should be distributed on the incubation surface Si by gravity, for a sufficient time for the reaction between the liquid and the components, in particular proteins, deposited on the gel, in particular by electrophoresis, to take place, at the end of the incubation, the extra liquid spread on the well-defined incubation surface of the gel is withdrawn via means arranged through the previously defined slit, in particular with the aid of filter paper, the mask is withdrawn from the gel.

The subject of the invention is also a method in which the mask is kept parallel with respect to the gel, and the set is inclined according to a sufficient angle with respect to the horizontal for the liquid to spread by gravity on the incubation surface Si, and advantageously according to an angle $\beta$ ranging from approximately 5° to approximately 90°, advantageously approximately 30°.

The invention also relates to a method in which the mask is kept according to a sufficient angle with respect to the gel for the liquid to spread by capillarity on the incubation surface Si, and in particular according to an angle $\alpha$ of approximately 0.5 to approximately 3°, advantageously approximately 1.5°.

A subject of the invention is an electrophoresis apparatus characterized in that it comprises a mask as previously described, intended for spreading and incubation of one or several reagents.

The invention can be illustrated in the light of the description which follows.

This new type of mask of the invention (floating mask or suspended mask) can be constituted by a flat and rigid piece of plastic which is preferably transparent (for example Plexiglas), having for example a thickness of approximately 2 to approximately 10 mm and in which the lower surface comprises at least one part Sm whose area corresponds at least to that of the surface of the gel to be covered by the reagent, also called "incubation surface Si". This piece of plastic is drilled right through and perpendicularly to its surface with a deposition orifice, preferably of elongated shape, situated inside or outside the incubation zone. This deposition orifice permits introduction of the reagents by means of a pipette.

The part Sm of the lower surface of the piece of plastic corresponding to the incubation surface is characterized by the fact that it has no surface irregularities (polishing). It is arranged by appropriate support means in proximity to the surface of the gel, either parallel thereto or slightly inclined, but without there being any contact between the incubation surface Si and the part Sm of the mask.

Given the small distance between the surface of the gel and the surface of the plastic (0.1 to 2 mm), the liquid introduced by means of a pipette through the deposition orifice is distributed by capillarity between the two flat surfaces (part Sm and surface of the gel) and covers the zone of the gel which is in projection beneath the part Sm of the piece of plastic.

The volume introduced must be at least equal to the volume V of the clear space between the two surfaces in order for the incubation surface Si to be covered.

Extra liquid (reagent) with respect to this volume V being able to be up to 1.2 or 1.3 times; the volume V being preferred. In fact, it permits covering of the gel according to the incubation surface Si to be assured even if a slight evaporation of the reagent takes place during the incubation phase.

In fact, this excess of reagent will be mainly kept by capillarity in the region of the deposition orifice, insofar as the latter has an elongated shape of small width (1 to 2 mm) (in order for capillary effects to develop there) and of a length which is sufficient (greater than or equal to 4 mm) to assure a sufficient volume of liquid kept by capillarity (see the examples hereinbelow).

If a quantity of reagent slightly greater ($\times 1.1$) then the sum of the volume V and the volume of liquid capable of being kept by capillarity in the region of the deposition orifice is added, through the deposition orifice, this excess will be distributed homogeneously at the periphery of the incubation surface of the piece of plastic, leading to a slight increase in the area of the surface of the gel subjected to incubation, but this occurs regularly, this excess always being kept in the region of the piece of plastic by capillarity.

In the case of using a single reagent, the only drawback is an unnecessary consumption of reagent.

In the case of incubation of adjacent zones with different reagents, it is sufficient for the spacing between the contiguous incubation surfaces to be sufficient to tolerate this increase in area of treated surface, without there being a risk of the surfaces treated by two different reagents becoming joined.

In any case, the separation between the zones must be greater than or equal to 2 or 3 mm, in order for the phenomena of diffusion of the reagents in the gel taking place during the incubation phase (5' to 30') not to lead to interactions between the various reagents which have diffused in the gel. In the case of longer incubation times, for example 1h, a spacing greater than or equal to 4 or 5 mm will be necessary, but this is equally true in the case of the other types of method previously used.

The elongated shape of the deposition orifice, in addition to its role, mentioned hereinabove, as a reserve of reagent, has the advantage of permitting easy introduction of the reagent onto the gel, for example by making the liquid flow on the vertical wall of the orifice, at one end of the latter.

In the case of a circular orifice of the same diameter as the width of the preceding orifice, it is necessary to assure a seal by friction between the tip of circular cross-section of the pipette and the orifice, and to inject the reagent onto the surface of the gel with a slight pressure, this pressure having a value such that it is equal to or greater than that necessary to overcome the capillary forces which develop in the region of the circular orifice of small cross-section. In this case, it is advantageous that the area of the surface Sm should be greater than Si and that the volume of the quantity injected should be less than the volume contained between the surface Sm and the gel.

The width of the deposition orifice is such that the end of the frustoconical tip of a pipette can penetrate therein, without however permitting it to descend beyond the plane of the surface of the plastic situation opposite the gel. The end of the pipette can therefore in no case damage the surface of the gel during introduction of the reagents.

Another advantage of the device of the suspended mask is that the phenomena of evaporation which can take place during the incubation are greatly reduced, since they can only take place at the periphery of the incubation surface and in the region of the deposition orifice.

After the incubation phase, it is expedient to remove the excess of reagent.

In the case where several reagents are used on contiguous zones, it is possible to proceed as follows.

The various incubation surfaces are generally rectangles whose long sides are parallel and whose short sides are colinear.

By making along these short sides a slit going from one side to the other of the piece of plastic, it is possible to introduce through the latter a piece of filter paper which is to be applied on to the gel and to be flush with the liquid kept between the plastic mask and the gel. By capillarity, the liquid rises into the filter paper and is removed via the incubation surface or surfaces.

However, in order to facilitate this removal of the liquid by pumping by means of filter paper, it is important for the suspended mask not to be perfectly parallel to the gel, but to make a dihedron with a very small angle, of 1° to 2°, the vertex of which dihedron is on the side where it is desired to pump the liquid through the filter paper. In fact, under these conditions, the capillary forces are stronger on the side where the gel/mask distance is smallest and the liquid interposed between these two surfaces has a tendency to collect therein and therefore to facilitate its removal through the filter paper, when the latter is introduced into the slit intended for this purpose.

FIGS. 1 & 1A

Single Useful Surface Mask/Incubation Surface

Figure 1:
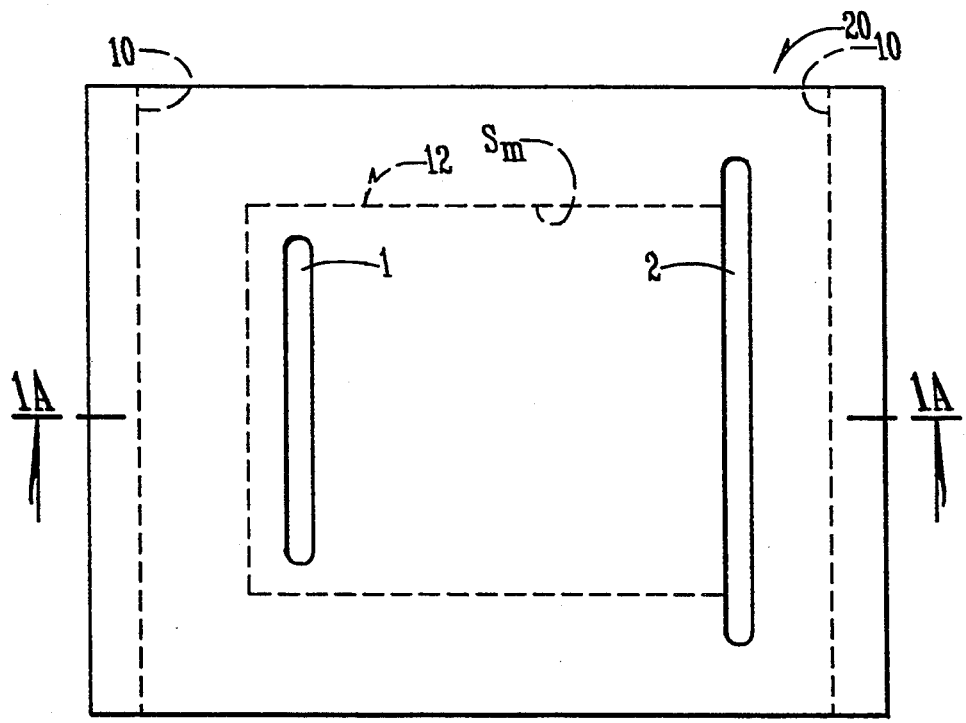
FIG. 1 is a plan view of the mask of this invention.
Figure 1A:
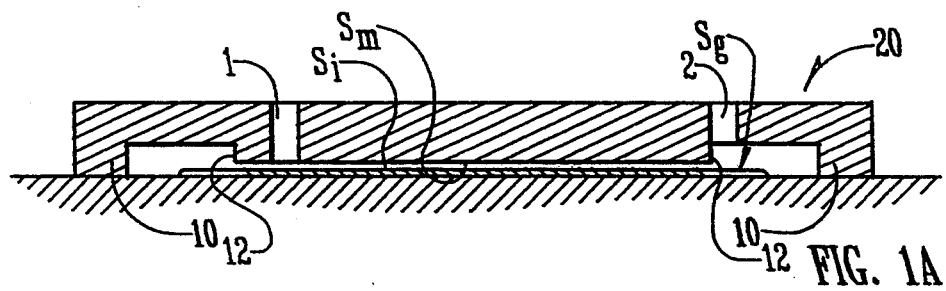
FIG. 1A is a cutaway view of the mask taken along line 1A—1A in FIG. 1.

In FIG. 1, the mask of this invention is shown and generally denoted by reference numeral 20. Sm represents the useful surface of the mask, delimited on one side by an elongated slit 2 and on each of the other three sides by a difference in disposed above a gel surface Sg having a single incubation surface Si by means of stops 10. As will be discussed later, the steps 12 and thereby the height of surface Sm above surface Si are selected to achieve the desired capillary action of liquids deposited therebetween. In the embodiment shown in FIGS. 1 and 1A, a single liquid reagent can be introduced on the incubation surface Si through deposition orifice 1. Thereafter, the reagent spreads by capillary action between surface Sm and the incubation surface Si. After incubation, the excess reagent is pumped out via slit 2. Of course, different reagents can also be applied in a consecutive fashion to incubation surface Si using this same mask.

Figure 2C:
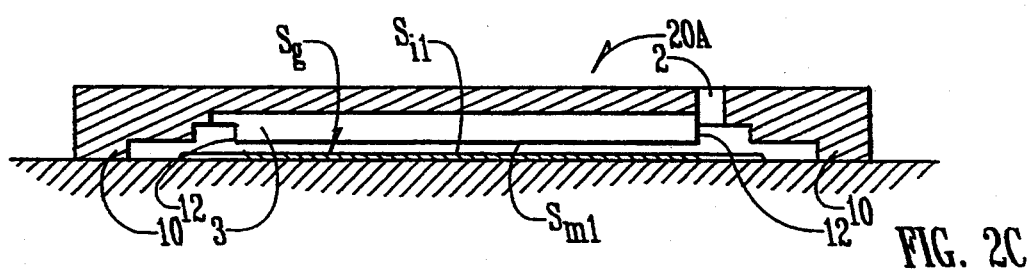
FIG. 2C is a cutaway view taken along line 2C—2C of FIG. 2 which shows the elongated groove, slit, and positioning means or stops of this invention.
Figure 2D:
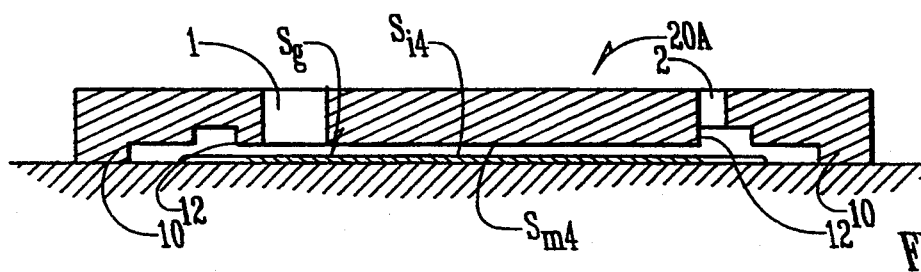
FIG. 2D is a cutaway view taken along line 2D—2D of FIG. 2 which shows the deposition orifice, slit and mask surface of this invention.

FIGS. 2, 2C and 2D

Plural Mask/Incubation Surfaces

FIG. 2 shows an embodiment of the present invention in which a single mask 20A is arranged to receive and separately deposit one or more liquids on several different incubation surfaces. Although any number of useful surfaces are achievable with this invention, FIG. 2 shows six different useful surfaces $Sm_1$-$Sm_6$ disposed for capillarity above six respective incubation surfaces $Si_1$-$Si_6$. Alternatively, this same mask 20A can be used to deposit a single reagent on each of the multiple incubation surfaces $Si_1$-$Si_6$. In either case, mask 20A has an elongated slit 2 intersected by a series of grooves 3 running across the bottom side of the mask. Grooves 3, slit 2, and steps 12 together delimit the useful surfaces $Sm_1$-$Sm_6$ of the mask which are therefore operatively positioned above the corresponding incubation surfaces $Si_1$-$Si_6$. The reagent or respective reagents are introduced to incubation surface $Si_1$-$Si_6$ via respective deposition orifices 1, with any excess being pumped out through slit 2 after incubation.

FIGS. 2C and 2D show the structure of mask 20A in greater detail. In FIG. 2C, a typical groove 3 is shown to extend below and adjacent to a typical useful surface $Sm_1$, thereby delimiting a side of surface $Sm_1$. The ends of a typical Sm, here $Sm_1$, are delimited by step 12 as previously discussed with respect to FIG. 1. FIG. 2D illustrates how a deposition orifice 1 is provided near the end of each useful surface $Si_1$-$Si_6$ opposite slit 2.

Figure 3A:
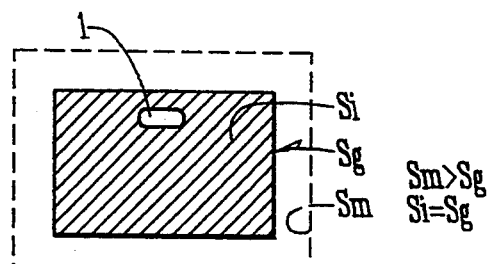
FIG. 3a is an illustration of a gel/mask set in which the area of the useful surface portion Sm of the mask is greater than both the incubation surface Si and the surface of the gel Sg.
Figure 3B:
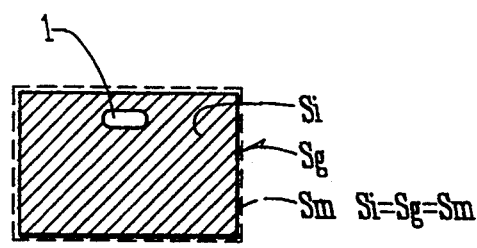
FIG. 3b is an illustration of a gel/mask set in which the area of the useful surface portion Sm of the mask is the same as that of the incubation surface Si and gel surface Sg.

FIGS. 3a & 3b

Gel/Mask Sets For Complete Gel Coverage

FIGS. 3a and 3b represent gel/mask sets for the deposition of a single reagent on the entire area of a gel surface Sg. The basic structure of the mask of these sets corresponds to FIG. 1. Therefore, it should be understood that the mask of this invention can be constructed to present any particular useful surface Sm area, depending on the placement of steps 12. Furthermore, it should be noted that the area of incubation surface Si depends not only on the area of useful surface Sm of the mask, but also on the area of the gel surface Sg. In FIGS. 3a and 3b, the periphery or perimeter of the useful surface Sm of the mask is shown as a dotted line. Deposition orifice i intersects useful surface Sm. The perimeter of gel surface Sg is shown in solid lines and the area of the incubation surface Si is hatched. FIG. 3a illustrates the situation where the mask/gel set is constructed so that the useful surface Sm of the mask is greater than the gel surface Sg. As a result, the area of incubation surface Si equals the area of gel surface Sg. Thus, the reagent can be deposited for incubation over whole gel surface Sg. The relationship between the various surface areas can be expressed by two equations:

Sm > Sg

Si = Sg

In FIG. 3b, the mask/gel set is constructed so that both the useful surface Sm of the mask and the area of incubation surface Si equals the area of gel surface Sg. The relationship between the various surface areas can be expressed by one equation:

$$Si = Sg = Sm$$

The slit 2 is not represented in FIGS. 3a and 3b, but should be understood from FIGS. 1 and 2 and the description thereof to be disposed opposite the deposition orifice 1 along the lower perimeter of Sm in the case of FIG. 3a or inside the perimeter of Sm and Si in the case of FIG. 3b.

Figure 4A:
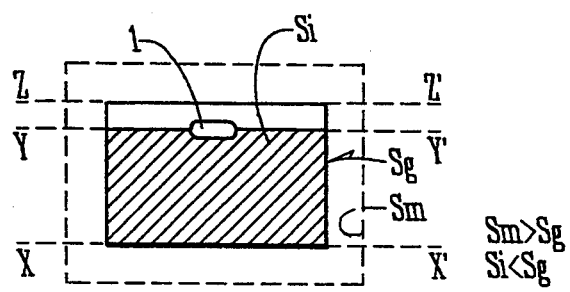
FIGS. 4a, 4b, and 4c are plan views showing possible relationships between the areas of surfaces Sm, Si, and Sg with this invention.
Figure 4B:
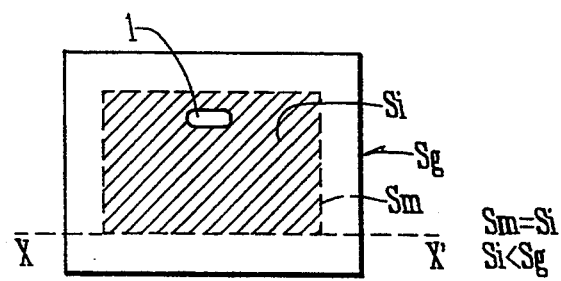
Figure 4C:
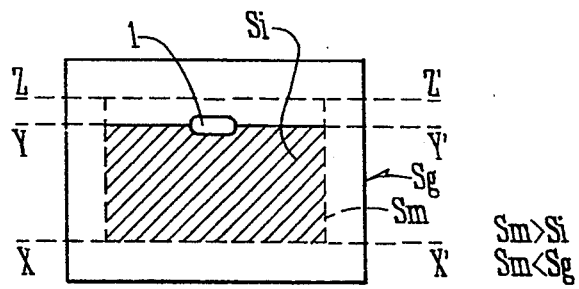

FIGS. 4a, 4b, & 4c

Gel/Mask Sets For Partial Gel Coverage

FIGS. 4a, 4b, and 4c represent gel/mask sets for depositing a single reagent on a portion of the gel surface Sg. In these cases, the incubation surface Si is smaller than gel surface Sg. Again, the perimeter of the mask useful surface Sm is shown by dotted lines, the perimeter of gel surface Sg is shown by solid lines, and incubation surface Si is hatched. The deposition orifice is denoted by reference numeral 1. Slit 2, through which excess liquid can be removed, has been omitted to avoid confusion, but is understood to be located adjacent to axis X—X' on one side or the other. Referring to FIG. 1, it is apparent that slit 2 can be located either inside or outside of the incubation surface Si depending upon which side of slit 2 is adjacent to step 12. The same results are achieved as long as the slit is dimensioned to ensure capillary action within Si.

FIG. 4a corresponds to the case where the mask/gel set is constructed such that the useful surface Sm of the mask is greater in area than either the area of the incubation surface Si or gel surface Sg. The incubation surface Si covers less than the entire gel surface Sg and deposition orifice 1 intersects the periphery of surface Si at the upper limit thereof as represented by line Y—Y'. The liquid is deposited in such a way that it covers only part of the gel surface, so that Si < Sg. Accordingly, this mask/gel set provides for the deposition of a single reagent on a portion of the gel surface Sg. Surface Si has a lower limit denoted by line X—X' and an upper limit denoted by line Y—Y'. The upper limit of gel surface Sg is shown by line Z—Z' above deposition orifice 1. The relationship between the various surface areas can be expressed by two equations:

$$Sm > Sg$$

$$Si < Sg$$

FIG. 4b corresponds to the case where the useful surface Sm of the mask is equal in area to the incubation surface Si, but smaller in area than gel surface Sg. Deposition orifice 1 is located inside the periphery of incubation surface Si. Again, line X—X' corresponds to the lower limit of Si. The relationship between the various surface areas can be expressed by two equations:

$$Sm = Si$$

$$Si < Sg$$

FIG. 4c corresponds to the case where the mask/gel is constructed such that the area of the useful surface Sm of the mask is greater than that of incubation surface Si, but less than that of gel surface Sg. Deposition orifice 1 is again disposed along line Y—Y' and below Z—Z' which denotes the upper limit Z—Z' of gel surface Sg. The liquid is deposited in such a way that it covers only part of the gel surface, so that Si < Sg. The relationship between the various surface areas can be expressed by two equations:

$$Sm > Si$$

$$Sm < Sg$$

It should be noted from FIGS. 3a, 3b, 4a, 4b, and 4c that the useful surface Sm of the mask determines the maximum possible area of incubation surface Si. When Sm is greater than Si, the deposition orifice 1 should be disposed at the upper limit Y—Y' of Si or inside Si to insure capillary flow of the reagent to incubation surface Si. Furthermore, it should be understood that slit 2 is located in the vicinity of line X—X'.

Figure 5A:
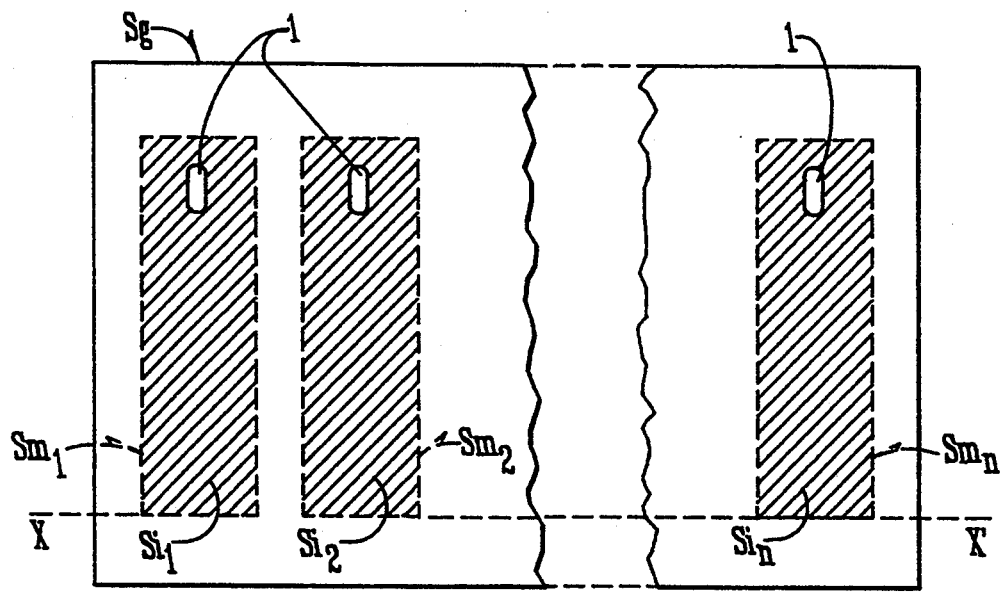
FIGS. 5a and 5b are plan views showing how several different reagents or a single reagent can be applied to several distinct incubation surfaces Si to Sn of the same gel.
Figure 5B:
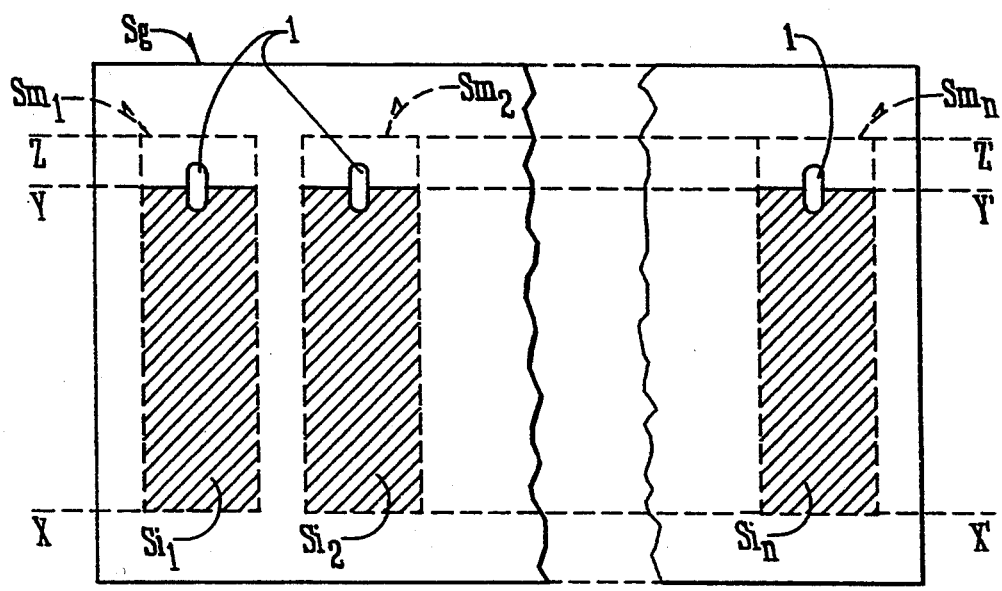

FIGS. 5a & 5b

Gel/Mask Sets for Several Distinct Incubation Zones

FIGS. 5a and 5b represent the case where the gel/mask set is constructed such that several different reagents or a single reagent can be deposited on several distinct incubation surfaces (shown hatched and denoted $Si_1$–$Si_n$) on the same gel surface Sg (shown in solid lines). The deposition orifices are designated by reference numeral 1. The useful surfaces $Sm_1$–$Sm_n$ are delimited by the dotted lines.

In FIG. 5a, line X—X' coincides with the lower limit of incubation surfaces $Si_1$ to $Si_n$. The area of gel surface Sg is greater than that of the individual and combined useful surfaces $Sm_1$ to $Sm_n$ of the mask. The area of individual surfaces $Sm_1$, $Sm_2$ ... $Sm_n$ is equal to that of the respective incubation surfaces $Si_1$, $Si_2$, ... $Si_n$. In equation form: Sm = Si.

In FIG. 5b, each mask useful surface $Sm_1$, $Sm_2$ ... $Sm_n$ has an upper limit denoted by line Z—Z'. Below line Z—Z', each incubation surface $Si_1$, $Si_2$, ... $Si_n$ has an upper limit Y—Y' which is established, independent of the mask, by the way in which the liquid is deposited. Line X—X' coincides with the lower limit of both the incubation surfaces $Si_1$, $Si_2$, ... $Si_m$ and the mask useful surfaces $Sm_1$, $Sm_2$, ... $Sm_n$. The relation between the mask useful surfaces and incubation surfaces can be expressed as Sm > Si.

As in FIG. 5a, the area of gel surface Sg is greater than the combined area of useful surfaces $Sm_1$, $Sm_2$, ... $Sm_n$. In an attempt to avoid confusion, slit 2 is not shown in FIGS. 5a and 5b.

FIGS. 6a–6i

Various Gel/Mask Sets

FIGS. 6a–6i are cutaway diagrams of various gel/mask sets according to this invention. As a point of reference, these views are similar to those shown in FIGS. 1A and 2D.

FIG. 6a corresponds to the case where useful surface Sm of the mask is constructed flat and positioned parallel to the horizontally disposed gel surface Sg. The distance separating surface Sm from incubation surface Si is constant and denoted by a lowercase e. The deposition orifice 1 for introducing the reagent is located adjacent one end of incubation surface Si and slit 2 for pumping out the excess liquid is disposed at the opposite end of Si. Slit 2 is slanted with respect to the useful surface Sm of the mask to facilitate easy removal of excess liquid from the incubation surface by pumping action with filter paper and the like. In conjunction with a difference in height or step 12, slit 2 delimits useful surface Sm. In the depicted case, the volume V of reagent to be introduced must be greater than or equal to Sm×e.

FIG. 6b corresponds to the case where surface Sm is constructed to be parallel to gel surface Sg, but the entire gel/mask is inclined at an acute angle $\beta$ for horizontal, preferably about 15°, such that slit 2 is disposed lower than deposition orifice 1. Thus, the capillary action is assisted by gravity. In this case, the volume V of reagent introduced must be greater than or equal to Si×e.

FIG. 6c corresponds to the case where the gel/mask set is constructed and arranged so that the gel surface Sg is horizontally disposed and useful surface Sm along with the mask is inclined at a small acute angle $\alpha$ therefrom, preferably approximately 1° to 2°, such that slit 2 is disposed slightly lower than deposition orifice 1. The minimum distance between Sm and Si is denoted by e1, and the maximum distance is denoted by e2. In this case, the volume V of reagent introduced is greater than or equal to $$Si \times \frac{(e1 + e2)}{2}.$$

FIG. 6d corresponds to the case where the mask is constructed with flat upper surface and a flat useful surface Sm, which form a dihedral having an acute angle y between them. The minimum and maximum distances between Sm and incubation surface Si are denoted by e1 and e2 respectively. In this case, the volume V of reagent introduced is greater than or equal to $$Si \times \frac{(e1 + e2)}{2}.$$

FIG. 6e corresponds to the case where the mask is constructed such that useful surface Sm is constituted by two flat surfaces S'm and S"m whose intersection is designated by the numeral 7. Surface S'm extends parallel to the horizontal gel surface Sg and surface S"m extends at an angle $\theta$ from S'm. The minimum e1 distance between surface Si and surface S'm occurs at the lower end of S"m, and the maximum distance e2 occurs along surface S"m. In this case, the volume V of reagent introduced is greater than or equal to $$(Si - S''m \cos \theta) e2 + S''m \cos \theta \frac{(e1 + e2)}{2}.$$

The above description applies when the incubation surface Si extends all the way to meet slit 2. However, it is equally possible to contemplate the incubation surface Si stopping below the intersection 7 of incubation surfaces S'm and S"m such as shown in FIG. 6f. In contrast to the situation shown in FIG. 6e, FIG. 6f shows a case where the volume of reagent spread per square unit of area on incubation surface Si is constant. For instance, the constant volume/area could be expressed in $\mu l/mm^2$.

A constant volume of reagent per incubation surface area is advantageous when the incubation is prolonged (because the incubation reaction kinetics are slow) or when the reagent introduced is in short supply with respect to the requirements of the reaction (perhaps because the reagent is relatively expensive). In order to achieve consistent results whatever the position of the incubation zone, it is important to have an equal distance between the gel and mask above the zone. In the example shown, the zone corresponding to the narrowing of the gel/mask space is subject to incubation. However, in practice it may be undesirable to subject the narrowing zone to incubation since this leads to slight over-consumption or wasting of the reagent.

FIG. 6g corresponds to the case where the mask is constructed with a flat surface Sm parallel to the horizontal gel surface Sg and a cylindrical surface S"m of radius R which is tangent to S'm. The incubation surface Si has a length Li. Radius R is of the same order of magnitude or greater than length Li. Deposition 1 and slit 2 are located as shown.

Figure 6H:
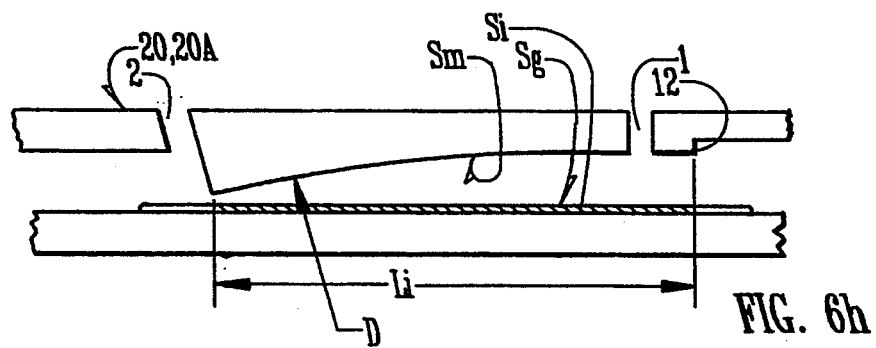
Figure 6I:
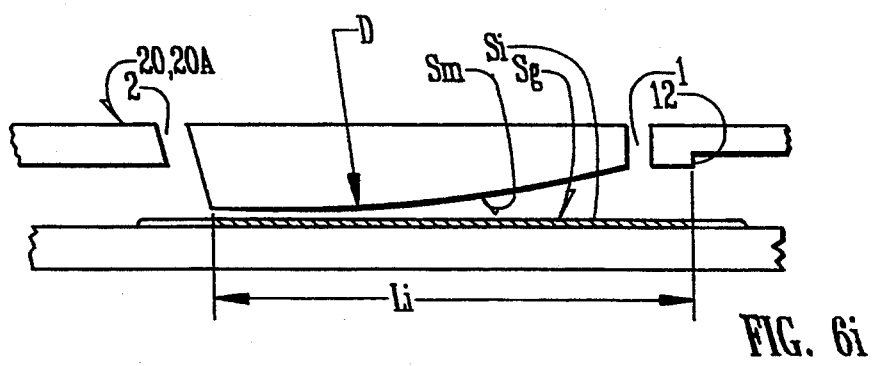

FIG. 6h and 6i both correspond to the case where the entire useful surface Sm is cylindrical. FIG. 6h shows the surface Sm constructed to be concave. Whereas FIG. 6i shows surface Sm to be convex. In both cases, the effective diameter D of the cylindrical lower surfaces is greater than the square of length Li.

Combined Deposition Orifice/Slit Gel/Mask Sets

Figure 7C:
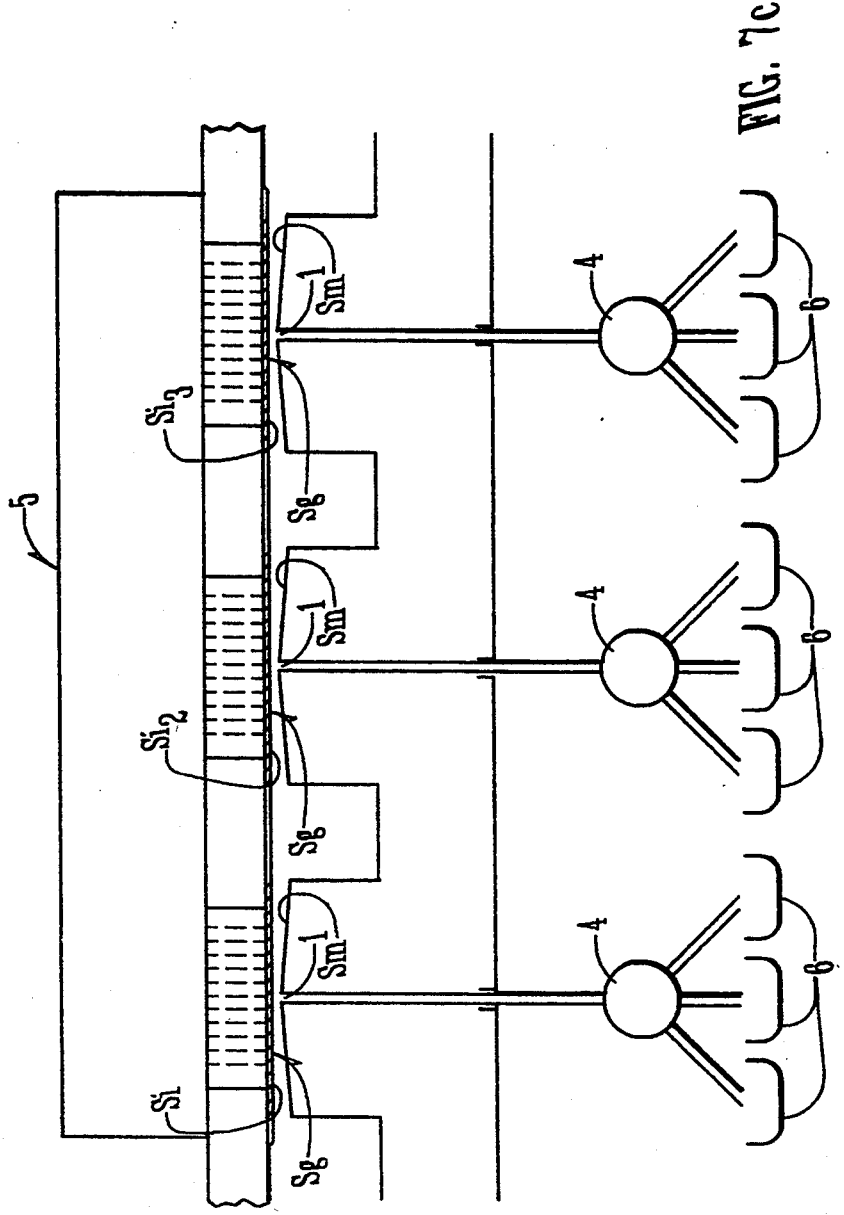

FIGS. 7a, 7b, and 7c illustrate a gel/mask set in which the mask is constructed so that the deposition orifice i also serves as the slit for removal of excess liquid after incubation. The gel surface Sg is poured onto a plastic support. The upper surface of the mask is parallel to gel surface Sg. The lower surface Sm of the mask is inclined upwardly with respect to gel surface Sg on either side of orifice 1. In FIG. 7a, the gel surface Sg is disposed beneath the mask.

FIG. 7b and 7c show a mask disposed below the gel surface Sg. The gel is held in close proximity above the mask without actually coming into contact therewith by a vacuum suction device 5. For example, a perforated plate connected to a vacuum supply tap can constitute the vacuum suction device 5. Note that the gel surface Sg faces downward and the "lower" useful surface Sm of the mask faces upward.

In FIGS. 7a, 7b, and 7c, one or more reagents are brought to orifice 1 for deposition and incubation by a pump 4 having one or more pipes drawing reagents from respective reservoirs. In fact, multiple channels or pipes are shown connected to respective reservoirs 6 such that various reagents can be pumped to each incubation surface $Si_1, Si_2, Si_3 \ldots Si_n$ in FIG. 7c.

EXAMPLES

EXAMPLE I

Mask intended for deposition, spreading and incubation of a single reagent on the whole of the surface of the gel Under these conditions, the surface of the gel can be either smaller than the surface Sm of the mask (FIG. 3a), or equal to the surface Sm of the mask (FIG. 3b).

When the gel is in a horizontal position and parallel to the lower surface of the mask, the distance between the gel and the mask is e. As a consequence the volume of reagent to be introduced is at least equal to Si×e=Sg×e.

EXAMPLES

When an excess of reagent is needed to compensate for losses due to evaporation during incubation, the excess over the requirements (according to the equation above) is distributed to the region of the deposition orifice if the orifice has dimension such that capillary forces can be developed. Otherwise, the extra reagent can be added periodically at the periphery of the incubation surface Si.

EXAMPLE II

Mask for deposition, spreading and incubation of a single reagent on a part of the gel It is possible to envisage the following configuration.

The surface Sm of the mask is greater than the incubation surface Si and the surface of the mask Sm is greater than or equal to the surface Sg of the gel, the deposition orifice being inside or outside the incubation surface Si (FIG. 4a).

If the gel and the mask are parallel to each other and separated by a distance e, the volume of reagent introduced is $Si \times e$.

In order to ensure the presence of the reagent on the incubation zone Si, the gel and mask set can be inclined by rotation around an axis parallel to X—X', so that the reagent descends under gravity from Y—Y' to X—X'.

In order to ensure covering of the incubation surface Si by the reagent, another possibility is to keep the gel in the horizontal position and slightly to incline the mask by rotation around an axis parallel to X—X', so that the gel/mask distance $e_1$ in the region of X—X' is less than the gel/mask distance $e_2$ in the region of Y—Y' (FIG. 6c). The capillary forces being stronger in the vicinity of X—X', the reagent is distributed by capillarity between X—X' and Y—Y'.

In this case, the mask then makes an angle $\alpha$ with the plane of the gel. If Li is the distance in mm between X—X' and Y—Y', $\tan\alpha$ is less than or equal to $$\frac{2}{Li}.$$

Under these conditions, the volume of reagent to be introduced in order to cover Si is:

$$\frac{Si(e_1 + e_2)}{2}$$

$e_1$ being greater than or equal to 0.1 mm because no contact must be created between the gel and the mask, $e_2$ being less than or equal to 2 mm in order for the capillary forces to be sufficient.

An excess of reagent, permitting compensation for the effects of evaporation which can be produced during the incubation, is distributed starting from Y—Y', between Y—Y' and Z—Z'.

EXAMPLE III

Mask for deposition, spreading and incubation of a single reagent on a part of the gel The surface Sm of the mask is equal to the incubation surface Si, and the surface Sm of the mask is smaller than the surface Sg of the gel, the deposition orifice being inside the incubation surface (FIG. 4b).

If the gel is in a horizontal position and is parallel to the mask, at the distance e, the volume of liquid to be introduced is $Si \times e = Sm \times e$.

A slight excess of reagent is distributed, either in the region of the deposition orifice, (if it has dimensions appropriate for capillary forces to develop therein) or, uniformly at the periphery of Si. In this case, it is not necessary to have to incline the gel and mask set or to create an angle between the plane of the gel and that of the mask.

EXAMPLE IV

Mask for deposition, spreading and incubation of a single reagent on a part of the gel The surface Sm of the mask is greater than the incubation surface Si, and the surface Sm of the mask is smaller than the surface Sg of the gel, the deposition orifice being along line Y—Y' at the edge of the incubation surface (FIG. 4c).

a) If the gel and the mask are parallel, separated by a distance e, the volume of reagent introduced is $Si \times e$.

In order to assure the presence of the reagent between X—X' and Y—Y', the gel and mask set is inclined by rotation around an axis parallel to X—X', so that X—X is in a lower position than Y—Y' and that the liquid descends by gravity to X—X' and collects between X—X' and Y—Y'.

The maximum angle allowable in order for the liquid to stay kept by capillarity between X—X' and Y—Y' increases as the distance e decreases. It can theoretically be 90°, for a distance e of 0.2 mm, in the case where the distance Li between X—X' and Y—Y' does not exceed 7.5 cm and if the reagent is water (Jurin's law).

b) If the gel is in a horizontal position, in order to assure the presence of the reagent between X—X' and Y—Y', the mask can be slightly inclined. This can be done so that the gel/mask separation $e_1$ in the region of X—X' is less than the separation $e_2$ in the region of Y—Y' (cf. Example II). The volume of reagent is then:

$$\frac{Si(e_1 + e_2)}{2}$$

EXAMPLE V

Case of distribution of several reagents, or possibly of the same reagent, but on several distinct incubation surfaces of the same horizontal gel with a mask parallel thereto The latter case (same reagent on several distinct surfaces) can be envisaged in order to limit consumption of the reagent.

If the gel and the mask are horizontal and parallel to each other, separated by a distance e, the volume of reagent to be introduced on to each incubation surface ($Si_1$ to $Si_n$) is $Si_1 \times e$, $Si_2 \times e$, etc. (FIG. 5a).

This example is similar to Example III.

EXAMPLE VI

Case of distribution of several reagents, or possibly of the same reagent, but on several distinct incubation surfaces of the same gel a) If the gel and the mask are parallel to each other, separated by a distance e, the conditions are similar to those of Example IVa.

b) If the gel is in a horizontal position and the mask is slightly inclined, the conditions are similar to those of Example IVb.

I claim:

1. A rigid mask for deposition, spreading and incubation of one or more liquids on a gel having one or more well-defined incubation surfaces Si thereon which each have a respective area defined by the product of a fixed length Li and width, said mask comprising:

an upper surface and a lower surface, the distance separating said upper and lower surfaces constituting the thickness of the mask;

said lower surface having a useful surface portion Sm which is delimited with respect to the remainder of the lower surface by surface irregularities on the lower surface which constitute obstacles to spreading of liquid by capillary action outside of Sm;

at least one deposition orifice extending through the thickness of the mask and intersecting the useful surface portion Sm for permitting deposition and spreading of the liquid on the incubation surface Si of the gel;

at least one slit extending through the thickness of the mask for permitting the subsequent withdrawal of any excess liquid present on the incubation surface Si of the gel, said slit having an opening intersecting the useful surface portion Sm of the mask, said opening being disposed opposite the incubation surface Si so as to be in fluid communication therewith;

means for positioning operatively mounted on said lower surface of the mask for positioning the mask with respect to the gel such that a minimum distance of at least 0.1 mm separates the useful surface portion Sm of the mask from the gel;

said useful surface portion Sm being smooth and devoid of any surface irregularity capable of being an obstacle to the spreading of the liquid between the incubation surface Si and useful surface portion Sm, such that the liquid can only spread on the surface Si of the gel which is a projection of Sm; and said useful surface portion Sm having a curvature with a diameter D at least equal to the square of the length Li of the incubation surface Si.

2. A rigid mask for deposition, spreading and incubation of one or more liquids on a gel having one or more well-defined incubation surfaces Si thereon which each have a respective area defined by the product of a fixed length Li and width, said mask comprising:

an upper surface and a lower surface, the distance separating the upper and lower surfaces constituting the thickness of the mask;

said lower surface having a useful surface portion Sm which is delimited with respect to the remainder of the lower surface by surface irregularities on the lower surface which constitute obstacles to spreading of liquid by capillary action outside of Sm;

at least one deposition orifice extending through the thickness of the mask and intersecting the useful surface portion Sm for permitting deposition and spreading of the liquid on the incubation surface Si of the gel;

at least one slit extending through the thickness of the mask for permitting the subsequent withdrawal of any excess liquid present on the incubation surface Si of the gel, said slit having an opening intersecting the useful surface portion Sm of the mask, said opening being disposed opposite the incubation surface Si so as to be in fluid communication therewith;

means for positioning operatively mounted on said lower surface of the mask for positioning the mask with respect to the gel such that a minimum distance of at least 0.1 mm separates the useful surface portion Sm of the mask from the gel;

said useful surface portion Sm being smooth and devoid of any surface irregularity capable of being an obstacle to the spreading of the liquid between the incubation surface Si and useful surface portion Sm, such that the liquid can only spread on the surface Si of the gel which is a projection of Sm; and said surface irregularities on the lower surface of the mask comprising two spaced apart grooves which delimit the useful surface portion Sm of the mask therebetween such that the area of said useful surface portion Sm is at least equal to the area of the respective incubation surface Si of the gel disposed opposite thereof, said grooves having sufficiently small height such that the liquid is held by capillarity on the respective incubation surface Si of the gel.

3. The mask of claim 2 wherein the gel has several incubation surfaces $Si_1$ to $Si_n$, n ranging from 2 to 50 and said surface irregularities on the lower surface comprise a plurality of spaced apart grooves delimiting therebetween a corresponding plurality of mask useful surface portions $Sm_1$ to $Sm_n$, n ranging from 1 to 50.

4. The mask of claim 2 wherein the deposition orifice has an elliptical shape.

5. The mask of claim 4 wherein said deposition orifice is approximately one to two millimeters wide and four to eighty millimeters long.

6. The mask of claim 4 wherein said deposition orifice is approximately one to five millimeters wide and five millimeters long.

7. The mask of claim 2 wherein said useful surface portion Sm of the mask is inclined witch respect to the gel surface at an angle α of approximately 0°-3° such that a minimum distance e1 exists between the useful surface portion Sm and the gel surface in the vicinity of the slit and a maximum distance e2 exists between the useful surface portion Sm and the gel surface in the vicinity of the deposition orifice.

8. A method of deposition, spreading and incubation of one or more liquid reagents on a gel surface Sg according to one or more well-defined incubation surfaces Si of the gel, comprising:

positioning adjacent to the gel a rigid mask having spaced apart upper and lower surfaces constituting a thickness therebetween, at least one deposition orifice for depositing and spreading of the liquid reagents on an incubation surface Si, at least one slit through said mask for permitting the withdrawal of liquid reagents, and positioning means for maintaining a minimum distance between the gel surface and a useful surface portion Sm of said lower surface of the mask, such that the useful surface portion Sm of the mask is sufficiently close to the incubation surface Si to allow the liquid reagents to be spread and retained by capillarity between the incubation surface Si and the useful surface portion Sm, said gel with the mask positioned adjacent thereto defining a gel/mask set;

introducing the liquid reagents into said deposition orifice;

inclining the mask to an angle α with respect to the gel surface which is sufficient to initiate distribution of the liquid reagents by capillarity on the surface Si;

holding said mask so positioned over the gel for a sufficient incubation time so that a reaction between the liquid reagents and the components deposited on the gel can take place;

at the end of the incubation, withdrawing the liquid reagents remaining on the incubation surface Si of the gel via said slit with the aid of filter paper; and withdrawing the mask from proximity with the gel.

9. The method of claim 8 wherein in said angle $\alpha$ is about 0.5° to 3.0° with respect to the gel.

10. The method of claim 9 wherein said angle $\alpha$ is approximately 1.5°.

11. A method of deposition, spreading and incubation of one or more liquid reagents on a gel surface Sg according to one or more well-defined incubation surfaces Si of the gel, comprising:

positioning generally parallel, and adjacent to the gel a rigid mask having spaced apart upper and lower surfaces constituting a thickness therebetween, at least one deposition orifice for depositing and spreading of the liquid reagents on an incubation surface Si at least one slit through said mask for permitting the withdrawal of liquid reagents, and positioning means for maintaining a minimum distance between the gel surface and a useful surface portion Sm of said lower surface of the mask, such that the useful surface portion Sm of the mask is sufficiently close to the incubation surface Si to allow the liquid reagents to be spread and retained by capillarity between the incubation Surface Si and the useful surface portion Sm, said gel with the mask positioned adjacent thereto defining a gel/mask set;

introducing the liquid reagents into said deposition orifice;

inclining the gel/mask set to an angle $\beta$ with respect to horizontal such that the liquid reagents spreads by capillarity on the incubation surface Si and said spreading is assisted by gravity;

holding said mask so positioned over the gel for a sufficient incubation time so that a reaction between the liquid reagents and the components deposited on the gel can take place;

at the end of the incubation, withdrawing the liquid reagents remaining on the incubation surface Si of the gel via said slit with the aid of filter paper; and withdrawing the mask from proximity with the gel.

12. The method of claim 11 wherein said angle $\beta$ ranges from approximately 5° to approximately 90°.

13. The method of claim 12 wherein said angle $\beta$ is approximately 30°.

* * * * *